(12) United States Patent
Pailloncy et al.

(10) Patent No.: US 9,791,484 B2
(45) Date of Patent: Oct. 17, 2017

(54) MEASUREMENT AND SYSTEM FOR PERFORMING A CALIBRATION

(71) Applicant: National Instruments Ireland Resources Limited, Dublin (IE)

(72) Inventors: Guillaume Pailloncy, Waasten (BE); Marc Vanden Bossche, Bornem (BE); Frans Verbeyst, Merchtem (BE)

(73) Assignee: National Instruments Ireland Resources Limited, Dublin (IE)

( * ) Notice: Subject to any disclaimer, the term of this patent is extended or adjusted under 35 U.S.C. 154(b) by 0 days.

(21) Appl. No.: 14/375,259

(22) PCT Filed: Feb. 11, 2013

(86) PCT No.: PCT/EP2013/052644
§ 371 (c)(1),
(2) Date: Jul. 29, 2014

(87) PCT Pub. No.: WO2013/117752
PCT Pub. Date: Aug. 15, 2013

(65) Prior Publication Data
US 2014/0368216 A1    Dec. 18, 2014

Related U.S. Application Data

(60) Provisional application No. 61/596,955, filed on Feb. 9, 2012.

(51) Int. Cl.
*G01R 27/02* (2006.01)
*G01R 25/00* (2006.01)
(Continued)

(52) U.S. Cl.
CPC ............ *G01R 25/00* (2013.01); *G01R 23/00* (2013.01); *G01R 27/02* (2013.01); *G01R 35/005* (2013.01);
(Continued)

(58) Field of Classification Search
CPC   G01R 27/02; G01R 27/2611; G01R 29/0821; G01R 29/0814; G01R 31/01;
(Continued)

(56) References Cited

U.S. PATENT DOCUMENTS

| 4,394,743 A * | 7/1983 | Mercer | ............... H04M 1/505 |
| | | | 341/147 |
| 7,362,826 B2 | 4/2008 | Willingham | |

(Continued)

OTHER PUBLICATIONS

Guillaume Pailloncy, et al., "Large-Signal Network Analysis Including the Baseband", IEEE Microwave Magazine, IEEE Service Center, Piscataway, NJ, US, vol. 12, No. 2, Apr. 1, 2011, pp. 77-86.

(Continued)

*Primary Examiner* — Huy Q Phan
*Assistant Examiner* — Raul Rios Russo
(74) *Attorney, Agent, or Firm* — Meyertons Hood Kivlin Kowert & Goetzel, P.C.; Jeffrey C. Hood

(57) ABSTRACT

The present invention relates to a method for calibrating a receiver device or a stimulus-response system comprising a receiver device. The method comprises the steps of
generating at least one tone with a repeatable and known phase value, said at least one tone being stepped in frequency to cover a given set of calibration tones, and applying the at least one tone to the receiver device or to the stimulus-response system,
generating a reference signal, which is phase-coherent with the at least one tone, to measure in a phase-coherent way with the receiver device or with the stimulus-response system the at least one tone,
measuring at least the phase of the at least one tone using the receiver device or the stimulus-response system,
determining at least phase-related information for calibration coefficients at the given set of calibration tones (Continued)

by calculating a phase deviation of the measured phase from the known phase value of the at least one tone.

22 Claims, 5 Drawing Sheets

(51) Int. Cl.
    *G01R 23/00* (2006.01)
    *G01R 35/00* (2006.01)
    *H04B 17/21* (2015.01)
    *G01N 27/64* (2006.01)
    *G01N 27/62* (2006.01)

(52) U.S. Cl.
    CPC .............. *H04B 17/21* (2015.01); *G01N 27/62* (2013.01); *G01N 27/64* (2013.01)

(58) Field of Classification Search
    CPC ......... G01R 35/00; G01R 23/00; G01L 21/30; G01N 27/62; G01N 27/64; H01J 41/00; H01J 41/02
    USPC ................... 324/76.11–76.83, 459, 600, 602
    See application file for complete search history.

(56) References Cited

U.S. PATENT DOCUMENTS

| | | | |
|---|---|---|---|
| 7,483,802 B2* | 1/2009 | Wood | H04B 10/588 356/237.1 |
| 2004/0061644 A1* | 4/2004 | Lier | H01Q 1/288 342/368 |
| 2005/0069056 A1* | 3/2005 | Willingham | H04B 17/21 375/327 |
| 2005/0219091 A1* | 10/2005 | Wood | H03M 1/1085 341/120 |
| 2007/0297523 A1* | 12/2007 | Cattaneo | H04L 27/2626 375/260 |
| 2009/0153132 A1* | 6/2009 | Tufillaro | H03F 1/3241 324/76.21 |
| 2009/0290517 A1* | 11/2009 | Rao | H01Q 3/267 370/280 |
| 2010/0018383 A1* | 1/2010 | Thirumoorthy | G10H 5/07 84/648 |
| 2010/0164782 A1* | 7/2010 | Saha | H04B 7/18515 342/174 |
| 2010/0184392 A1* | 7/2010 | Largey | H04B 17/21 455/115.2 |
| 2012/0082251 A1* | 4/2012 | Vanden Bossche | G01R 13/0272 375/259 |
| 2012/0295548 A1* | 11/2012 | Dunsmore | H04B 17/21 455/67.16 |

OTHER PUBLICATIONS

Philip Vael, et al., "A Controllable Phase Coherent Pulsed RF Signal Generator for Microwave Network Analyzer Measurements", IEEE Transactions on Microwave Theory and Techniques, IEEE Service Center, Piscataway. NJ. US, vol. 47, No. 12, Dec. 1, 1999, pp. 2605-2612.

* cited by examiner

MEASUREMENT AND SYSTEM FOR PERFORMING A CALIBRATION

FIELD OF THE INVENTION

The present invention is generally related to the field of radio frequency (RF) and microwave measurement technology. More in particular, it relates to calibration techniques for receivers and stimulus-response systems so that a signal and a device under test, respectively, can be characterized in an accurate way.

BACKGROUND OF THE INVENTION

A receiver device operating at RF and microwave frequencies is not perfect. For instance the frequency response of its input channels is not ideal: the amplitude varies as function of frequency and the phase is not perfectly linear as a function of frequency. Also, the input impedance of these channels deviates from the nominal value (typically, but not necessarily 50 Ohm). In order to perform accurate measurements of unknown signals, such receiver device has to be calibrated by applying an appropriate well known signal at one or more input channels. Comparing the signal as measured by the receiver device to the known signal allows compensating for the receiver imperfections. This compensation possibly includes the effect of the input impedance and possibly cables, adapters and other means required to connect to a signal or device under test that needs to be measured.

A receiver device can be used as part of a stimulus-response system, which is used to accurately characterize a device under test. Such systems allow taking advantage of the a priori knowledge of the signals being applied. These stimulus-response systems, such as sampler-, scope- or mixer-based network analyzers, require calibration techniques in order to perform accurate measurements at one or more defined calibration planes, typically the input(s) and output(s) of the device under test (DUT). Example stimulus-response systems such as Large-Signal Network Analyzers (LSNA) or Non-linear Vector Network Analyzers (NVNA), combine an appropriate relative calibration and a power and phase calibration in order to accurately measure voltage and current (or incident and reflected waves) in amplitude and in phase at the DUT ports, at all relevant frequencies (for instance, at the fundamental frequency and at the relevant harmonics or in case of a multi-tone excitation at all fundamental tones, relevant harmonics and intermodulation products). Note that with relative calibration technique is meant that only the ratios of wave quantities (or corresponding voltage and current) at identical frequencies are calibrated.

During power calibration, a calibrated power sensor is connected to one of the calibration planes (or an auxiliary calibration plane in case of on-wafer or in-fixture measurements).

During phase calibration, a calibrated pulse generator (in the art also referred to as comb generator, phase reference or harmonic phase reference) with stable and known phase relationship between its spectral components, after eliminating an arbitrary delay, is connected to one of the calibration planes (or an auxiliary calibration plane in case of on-wafer or in-fixture measurements). This pulse generator generates at least all tones (frequency components), typically harmonics of a common low-frequency tone $f_0$, for which the stimulus-response system needs to be calibrated. It can generate these tones simultaneously or in two or more steps, whereby each of the steps contains overlapping tones to stitch the steps together. The source driving the pulse generator must have at least a stable frequency and phase while the receivers of the network analyzer are measuring its response in a phase-coherent way. Amongst others, these pulse generators can be step-recovery-diode-based (SRD) and/or based on nonlinear transmission lines (NLTL) or based on high-speed logic.

FIG. 1 illustrates a conventional system as known in the state of the art. Two frequency-coherent sources are shown. One of the frequency-coherent sources generates a tone at a frequency $n.f_0$, which is applied to a pulse generator (depicted as a comb generator in FIG. 1) which produces phase-coherent tones at the calibration plane of the one-port analyser. The second source, which is connected to the receiver, is used in the receiving process]. Typically the measured signal is downconverted from RF to IF (intermediate frequency) using a mixer. The second source is applied internally in the receiver to the LO (local oscillator), which is typically common to all the mixers.

As an example a fundamental frequency $f_0$ is chosen to be 100 MHz. In order to generate phase-coherent tones at $m.100$ MHz (with $m=1, 2, \ldots, 670$) one can apply a single tone at $n.100$ MHz to a state-of-the-art comb generator, which simultaneously and therefore phase-coherently generates all tones. This is the tone generating part. Its output is measured by a frequency-coherent receiver through signal separation hardware which allows measuring the voltage and the current or the incident and reflected wave or any combination of these quantities. The processor shown in the figure gets the measured data and determines the calibration coefficients during the calibration process. Afterwards the processing means is used to apply these calibration coefficients as part of the measurements. Typically the processor is part of the stimulus-response system, but calibration coefficients can also be extracted (and afterwards applied) using an external processing means (e.g. an external PC or laptop).

Patent application US2009/125264 presents a technique for eliminating the systematic measurement errors from a measurement system for characterizing non-linear devices. A relative and an absolute error correction are performed and the results are adapted into an error correction model. Raw measured voltage waves from the device under test are then corrected using the error correction model. The cross-frequency phase and absolute amplitude of the measured voltage waves applied to and emanating from the non-linear device are measured and error corrected with the model.

Hence, there is a need for a solution where a stimulus-response system like a network analyzer can be calibrated in a more efficient way.

SUMMARY OF THE INVENTION

It is an object of embodiments of the present invention to provide for a method and system for calibrating a receiver device or a stimulus-response system comprising a receiver device, whereby the need for a separate pulse generator or phase-coherent multi-tone generator during the calibration process is avoided.

The above objective is accomplished by the solution according to the present invention.

In a first aspect the invention relates to a method for calibrating a receiver device or a stimulus-response system comprising a receiver device. The method comprises the steps of generating at least one tone with a repeatable and known phase value, said at least one tone being stepped in frequency to cover a given set of calibration tones, and applying the at least one tone to the receiver device or to the stimulus-response system, generating a reference signal, which is phase-coherent with the at least one tone, to measure in a phase-coherent way with the receiver device or with the stimulus-response system the at least one tone, measuring at least the phase of the at least one tone using the receiver or the stimulus-response system, determining at least phase-related information for calibration coefficients at the given set of calibration tones by calculating a phase deviation of the measured phase from the known phase value of the at least one tone.

By applying and measuring the at least one tone in a phase-coherent way, the at least one tone being stepped in frequency to cover the given set of calibration tones, it is indeed possible to avoid the use of a separate pulse generator or phase-coherent multi-tone generator during the calibration process. It is no longer needed to have the set of calibration tones present simultaneously in order to achieve repeatable phase relationships between the different calibration tones. The phase-coherent measurement of the at least one tone by the receiver can be achieved in various ways, either directly or indirectly. The calibration method can be used for calibrating either a receiver device or a stimulus-response system comprising a receiver device. The phase-coherent measurement of the at least one tone by the receiver yields several advantages. If the stimulus-response system includes phase-coherent sources as part of the stimulus (and receiving) part, these can be used during calibration. One no longer requires expensive additional hardware (i.e. a calibrated pulse generator). Also, the frequency range of the set of calibration tones automatically covers the frequency range of the stimulus-response system (and is not limited to the usable bandwidth of the pulse generator or phase-coherent multi-tone generator). Furthermore, the typical roll-off with increasing frequency of the amplitude spectrum of a calibrated pulse generator is no longer an issue.

The invention equally applies to receiver devices which can have one or more input channels. Example receiver devices are real-time and equivalent-time oscilloscopes and vector signal analyzers (VSA). Indeed, receiver devices are a simplified version of a stimulus-response system, where the signal separation corresponds to the input connector.

In a preferred embodiment the method comprises a step of applying the calibration coefficients to process measured signals.

In an embodiment at least two tones are generated with repeatable and phase-coherent phase value by means of distinct phase-coherent sources.

In an advantageous embodiment the reference signal is generated by means of a phase-coherent source.

In another aspect the invention relates to a calibration system for calibrating a receiver device or a stimulus-response system comprising a receiver device. The calibration system comprises synthesizing means adapted for generating at least one tone with a repeatable and known phase value, for stepping the at least one tone in frequency to cover a given set of calibration tones and for applying the at least one tone to the receiver device or to the stimulus-response system. This portion of the synthesizing means will be referred to as "tone generation" portion. The synthesizing means is further arranged for generating a reference signal, which is phase-coherent with said at least one tone. The calibration system further comprises processing means arranged for determining at least phase-related information for calibration coefficients at the given set of calibration tones by calculating a phase deviation between a measured phase and the known phase value of the at least one tone.

In one embodiment the tone generation portion of the synthesizing means comprises a plurality of synthesizers.

In an embodiment the calibration system comprises means for generating frequency tones in a simultaneous and phase-coherent way. Such means can be, for example, a coupler or a power combiner.

In another embodiment the calibration system further comprises a comb generator or any other means to generate phase-coherent tones connected between the reference signal and an available input channel of the receiver device, whereby this generator means achieves phase-coherent operation of the receiver with respect to the reference signal.

In a more specific embodiment the synthesizing means is part of the stimulus-response system. Further, in some embodiments of the invention, the processing means is part of the stimulus-response system. In yet other embodiments both the synthesizing means and the processing means are part of the stimulus-response system. It is repeated, however, that in other embodiments the synthesizing and/or the processing means are stand-alone devices.

In certain embodiments the receiver device of the stimulus-response system is arranged for operating phase-coherently with the synthesizing means.

In other embodiments the synthesizing means is arranged for operating phase-coherently with the receiver device as part of a stimulus-response system. In this case the receiver device provides the reference signal which then can be used by the synthesizing means to generate at least one tone which is phase-coherent with respect to the reference signal.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiments) described hereinafter.

BRIEF DESCRIPTION OF THE DRAWINGS

The invention will now be described further, by way of example, with reference to the accompanying drawings, wherein like reference numerals refer to like elements in the various figures.

DETAILED DESCRIPTION OF ILLUSTRATIVE EMBODIMENTS

Figure 1:
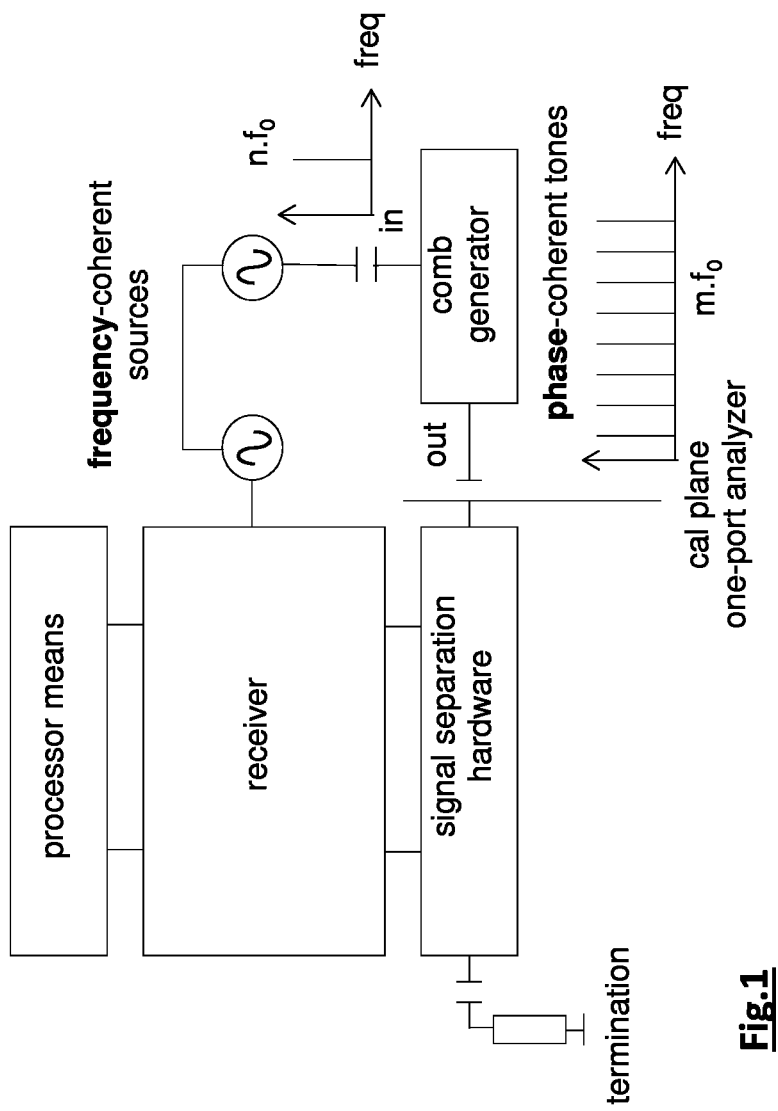
FIG. 1 illustrates a prior art solution wherein a pulse generator (also referred to as a comb generator) is applied.

The present invention will be described with respect to particular embodiments and with reference to certain drawings but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

The present invention capitalizes on the observation that a constellation of independent phase-coherent sources allows applying and measuring different frequencies, which have a repeatable phase relationship so that the need to apply these tones simultaneously is avoided. The invention requires such phase-coherent sources. State-of-art vector network analyzers nowadays have a plurality of independent phase-coherent sources. One example is the Rohde & Schwarz 4-port ZVA67 network analyzer which has four such sources.

Figure 5:
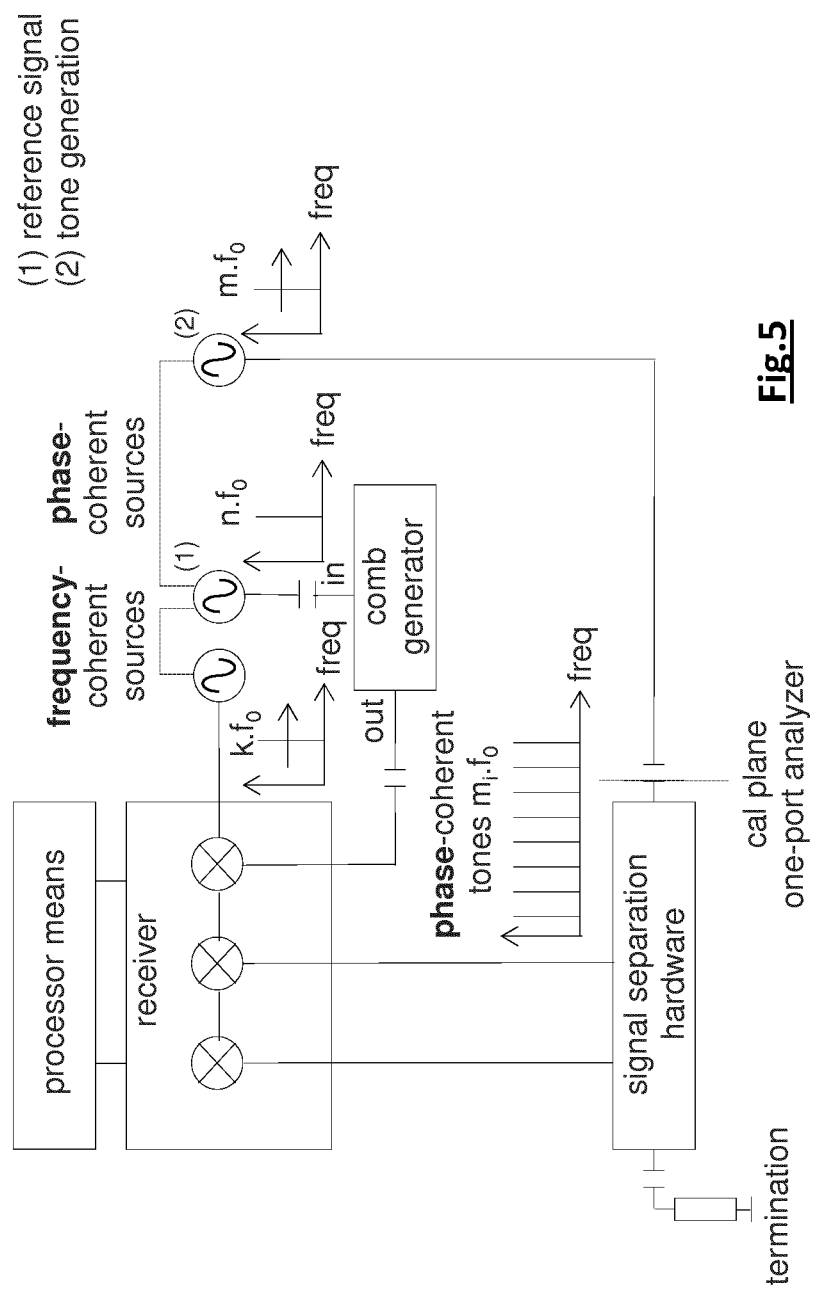
FIG. 5 illustrates an embodiment with two phase-coherent sources and a comb generator applied to an available input channel of a mixer-based receiver, the latter using a frequency-coherent source as part of the downconversion (instead of a phase-coherent source).

Absolute calibration means that both the amplitude and the phase of wave quantities (or corresponding voltage and current) at relevant frequencies are calibrated. The present invention proposes the use of independent phase-coherent sources or other realizations of phase-coherence capability (such as shown in FIG. 5) as a part of the absolute calibration of a stimulus-response system. A major advantage of this phase-coherent approach is that for the user the need is eliminated for a pulse generator or other means to generate simultaneously phase-coherent tones. The same holds for the calibration of a receiver device. In case of a trigger-based receiver device, a reference signal of the synthesizing means (possibly combined with other means such as a clipping amplifier) is applied as trigger signal, while the tone generation portion of the synthesizing means (possibly also combined with other means to simultaneously generate more than one tone) is applied to one or more inputs of the receiver.

The invention envisages solutions for calibrating stimulus-response systems with at least one measurement port. The system for calibrating a stimulus-response system according to the invention comprises a synthesizing means, which generates both a reference signal and at least one tone in a phase-coherent way. The at least one tone can be generated by one or more synthesizers. In the latter case they are typically combined with a power combiner, coupler or any other means capable of simultaneously generating a plurality of phase-coherent tones. In case a subset of tones at $m.f_0$ is used in the calibration process, the tone generation portion of the synthesizing means is advantageously combined with one or more components, such as, but not limited to, a pulse generator, arbitrary function or waveform generator, mixer or a diode or amplifier driven in its non-linear mode of operation. This allows a phase-coherent and repeatable generation of the subset of required calibration tones at $m.f_0$.

The proposed solution requires a receiver which operates phase-coherently with respect to the generated tones, where the fundamental frequency $f_0$ can be infinitesimally small (limited by the practical implementation of the synthesizing means) and where m can be any discrete set of integer numbers (m can be—but does not have to be $-1, 2, \ldots, M$). The given set of calibration tones is realized and measured by stepping the receiver phase-coherently with the at least one tone. Due to the phase-coherent operation no overlapping tones are required.

In one embodiment of the invention the stimulus-response system includes the processing means to acquire the calibration data, to extract the calibration coefficients and to apply these calibration coefficients as part of the signal processing.

Figure 2:
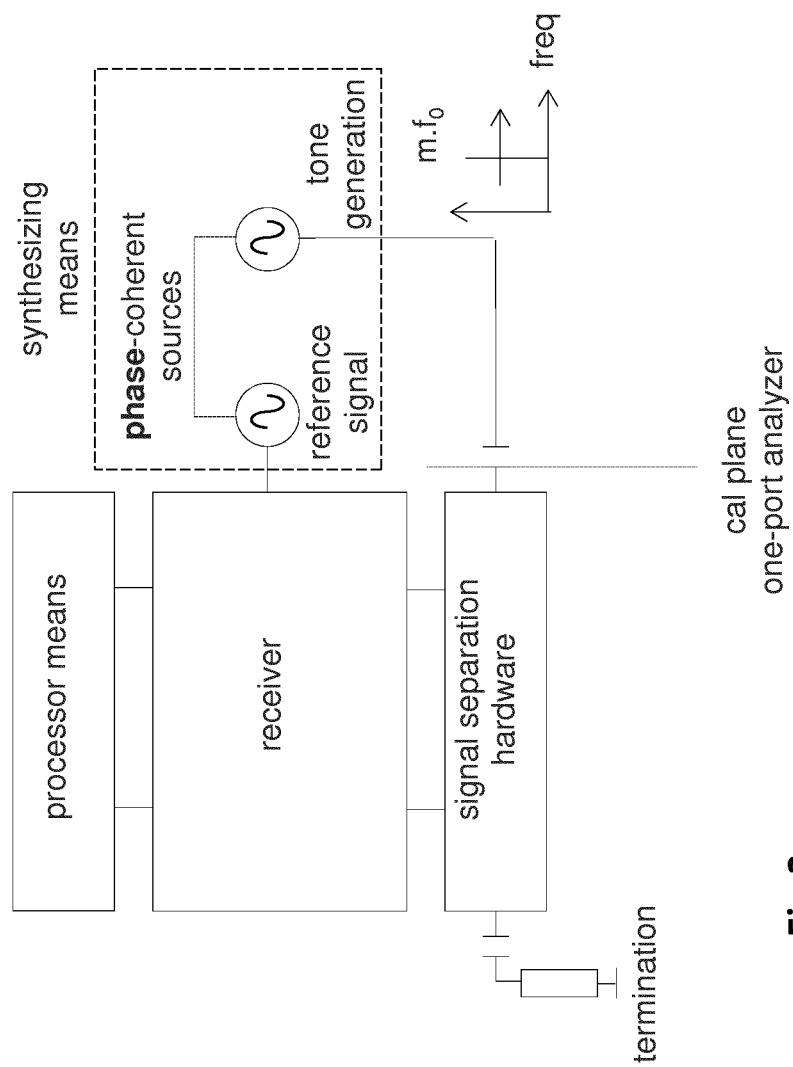
FIG. 2 illustrates an embodiment of the present invention.

A simple embodiment of the invention is shown in FIG. 2. As compared to FIG. 1, the comb generator is now replaced by phase-coherent synthesizing means. One tone $m.f_0$ is generated at a time and stepped in frequency with a repeatable and known phase value to cover a given set of calibration tones. Meanwhile a reference signal, phase-coherent with the one tone, is applied to the receiver, allowing the latter to measure the one tone in a phase coherent way.

Revisiting the already presented example with $f_0=100$ MHz, the synthesizing means generates a single tone at m.100 MHz (with m=1, 2, . . . , 670) as part of its tone generation portion and a phase-coherent reference signal which allows the receiver to operate phase-coherently with respect to each generated tone.

Figure 3:
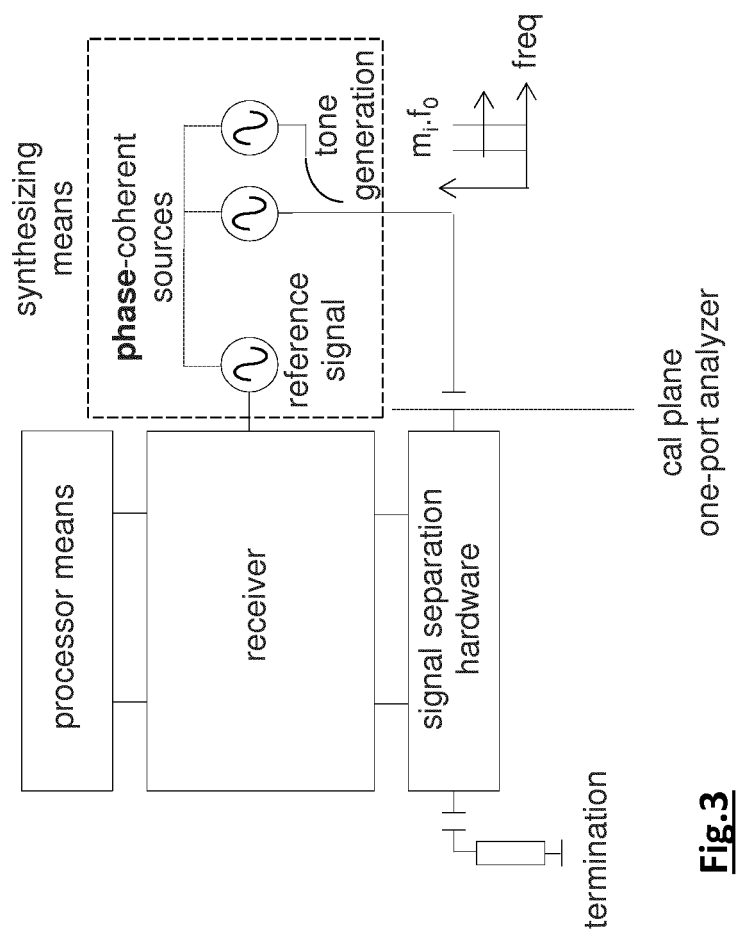
FIG. 3 illustrates an embodiment of the invention with two phase-coherent sources, simultaneously generating two tones of the given set of calibration tones.

In another embodiment the approach is to simultaneously generate a subset of the given tones. This is illustrated in FIG. 3. In this embodiment the comb generator of FIG. 1 is replaced by a synthesizing means, its tone generation portion comprising two phase-coherent synthesizers which in the above-mentioned example generate by means of a coupler two tones at $m_i.100$ MHz (where $m_i=\{1, 2\}$, $\{3, 4\}$, . . . , $\{669, 670\}$) at a time. The synthesizing means also provides a phase-coherent reference signal which allows the receiver to measure each generated pair of tones in a phase-coherent way.

Phase coherence between different sources can be achieved in several ways. One advantageous option is to apply a direct-digital synthesis (DDS) based technique. DDS is a well-known technique in the art of frequency synthesis.

One of the assets of the proposed solution is its independency of the concrete implementation at the receiver side, as long as the synthesizing means and the receiver operate phase-coherently, either directly or indirectly.

At the receiver side different configurations are possible. Although other receiver means are possible, some advantageous receiver implementations are based on a sampler-based receiver using the phase-coherent reference signal as provided by the synthesizing means as local oscillator (LO), while other preferred implementations can be based on a mixer-front-end with different possible configurations.

Figure 4:
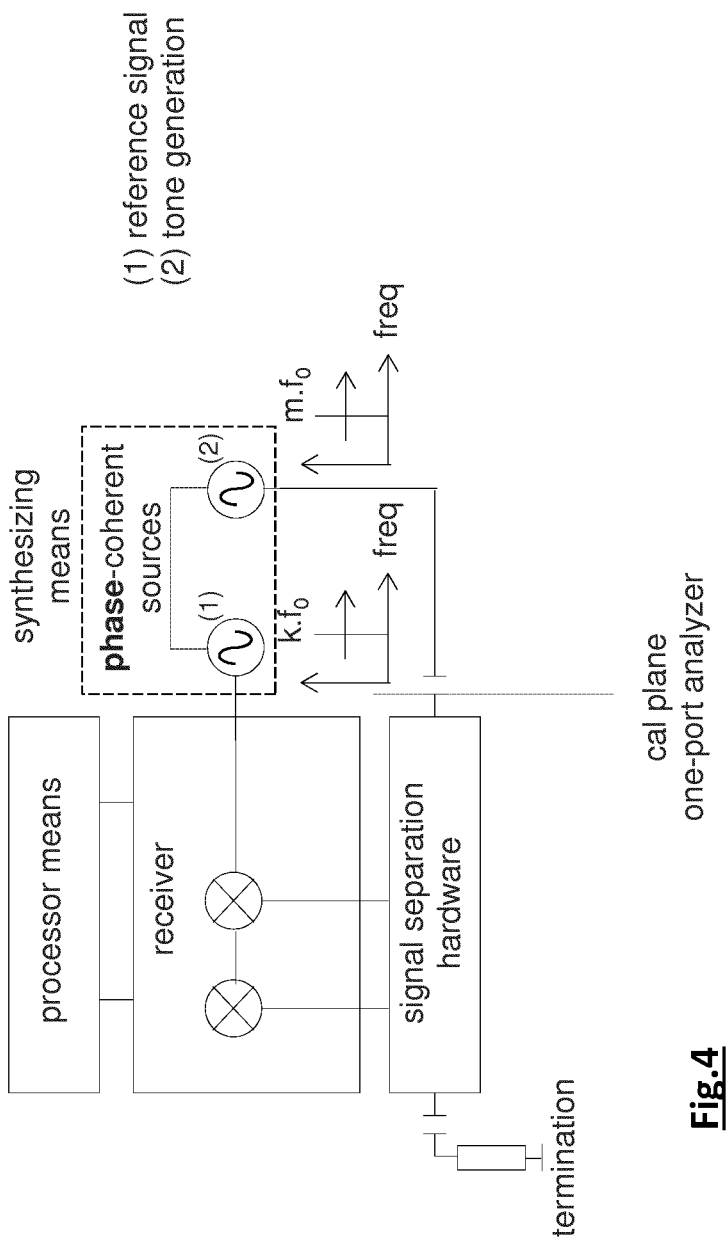
FIG. 4 illustrates another embodiment of the invention.

One possible configuration is based on a mixer-based receiver in combination with a synthesizing means generating a tone at frequency $m.f_0$ with specified phase. The phase-coherent reference signal at $k.f_0$ as provided by the synthesizing means is used to downconvert the applied calibration tone in a phase-coherent and repeatable way. Stepping the reference signal and as such the receiver frequency phase-coherently with the generated tone, all tones are covered at which the DUT or the receiver device must be characterized and as such, at which the stimulus-response system or the receiver device needs to be calibrated (FIG. 4).

Another advantageous configuration is based on a mixer-based receiver in combination with a synthesizing means and a comb generator (or another non-linear device). The latter does not have to be calibrated. FIG. 5 represents this embodiment. The tone generation portion of the synthesizing means is used to apply a tone at frequency $m.f_0$ with specified phase. The phase-coherent reference signal as provided by the synthesizing means is used to apply a tone at a fixed frequency $n.f_0$ to the input of the comb generator. The output of this comb generator is connected to an extra receiver input channel which is used as reference channel. The measurements performed by this channel are then used to provide phase coherence between the different tones $m.f_0$ measured at the other receiver input channels in combination with the fact that the measurements at a fixed tone are phase-coherent across the different receiver channels. As such, in this case the downconversion itself by the receiver at $k.f_0$ does not have to be phase-coherent with the applied tone at $m.f_0$. It has to be frequency-coherent instead. By stepping m, all tones are covered at which the DUT or receiver device must be characterized and as such at which the stimulus-response system or receiver device needs to be calibrated (FIG. 5).

Other configurations, which include a mixer- or sampler-based receiver or other receiver means, allow measuring more than one and possibly all tones at the (same) time in a phase-coherent way.

The stimulus-response system can be realized using one or more instruments. Typically the stimulus-response system uses one or more sources, a signal separation unit, a receiver unit (which can be built up of one or more units, e.g. a first downconversion stage from RF to IF and then using a separate digitizer). All these units can, but do not have to be integrated in one apparatus. Possibly sources are integrated as part of the stimulus-response system, but in certain embodiments of the invention it may be necessary to use additional external sources.

The solution according to the invention also allows replacing the calibrated power sensor required as part of the power calibration by exploiting the knowledge of the power of the applied tones. State-of-the-art calibration techniques do not use the power of the tones generated by the calibrated comb generator due to the limited power and the uncertainty on the power of each tone. The tones applied in the proposed solution do not have this problem.

The tone generation portion of the synthesizing means can be calibrated at manufacturing time and re-calibrated by the manufacturer (or end-user) when required. One advantageous calibration method among the various possible methods is explained here.

First a "classical" and well-known absolute calibration (i.e. comprising a relative calibration, a power calibration and a phase calibration) of an N-port network analyzer is performed (N≥1) where a "classical" phase reference (a calibrated comb generator) is applied during phase calibration.

Next the output of the tone generation portion of the synthesizing means is connected to one of the calibrated ports terminated at the other side by a proper, possibly varying, impedance.

Next the tone generation portion of the synthesizing means is set to $m.f_0$, one frequency at a time. At the same time the phase-coherent reference signal as provided by the synthesizing means and applied to the receiver is set to $k.f_0$ (FIG. 4) (or fixed to $n.f_0$ in case a non-calibrated comb generator is used to guarantee phase-coherent measurements (FIG. 5)) and the amplitude and phase of the calibrated incident and reflected wave (or voltage and current) is measured for the specified output level and phase of the tone generation portion of the synthesizing means. The difference between the specified and measured quantities results in a correction table to obtain a calibrated synthesizing means.

The impedance of the output of the tone generation portion of the synthesizing means is also measured using any appropriate method including—but not limited to—hot-$S_{22}$ parameters, X-parameters™ or S-functions.

This allows calculating the voltage into 50 Ohm and taking into account the effect of a non-50 Ohm load.

If mismatches turn out to be negligible, the calibration process can be simplified and the output of the tone generation portion of the synthesizing means can be directly connected to a receiver channel, which is calibrated with respect to power and phase.

If the phase relationship of the involved phase-coherent synthesizers is dependent on the output power, this dependency on the output power is properly taken into account by an additional simple calibration.

If an additional cable or other linear network is required between the calibrated output of the synthesizing means and the calibration plane when the synthesizing means is used as part of the phase calibration, this can be taken into account using standard (de)embedding techniques using the two-port S-parameters of this network.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for calibrating a system, the method comprising:
generating, by a synthesizer circuit, a set of calibration tones, comprising generating one tone of the set of calibration tones at a time with a repeatable known phase value and a different frequency value with respect to a most recent previously generated tone, and applying each generated tone to the system one tone at a time;
generating, by the synthesizer circuit, a reference signal, which is phase-coherent with each generated tone, to measure each generated tone in a phase-coherent way with the system;
measuring at least a respective phase of each generated tone using the system; and
determining, by a processor circuit, at least phase-related information for a set of calibration coefficients corresponding to the set of calibration tones, comprising calculating a phase deviation of the measured respective phase from the repeatable known phase value for each generated tone.

2. The method of claim 1, further comprising:
applying one or more calibration coefficients of the set of calibration coefficients to process measured signals.

3. The method of claim 1, further comprising:
generating at least one additional set of calibration tones in a simultaneous and phase-coherent way with the set of calibration tones.

4. The method of claim 3, wherein each tone of the set of calibration tones and the at least one additional set of calibration tones are generated by one or more of:
distinct phase-coherent sources;
a phase-coherent source driving at least a nonlinear device; or
an arbitrary waveform generator.

5. The method of claim 1, wherein the reference signal is generated by a phase-coherent source.

6. A calibration system for calibrating a first system, the calibration system comprising:
a synthesizer circuit configured to:
generate a set of calibration tones one tone at a time with a repeatable known phase value and a different frequency value with respect to a most recent previously generated tone; and
generate a reference signal which is phase-coherent with each generated tone; and
a processor circuit configured to:
apply each generated tone to the first system, one tone at a time; and
determine at least phase-related information for a set of calibration coefficients corresponding to the set of calibration tones by calculating a phase deviation between a respective measured phase of each generated tone and the repeatable known phase value.

7. The calibration system of claim 6, wherein the synthesizer circuit comprises a plurality of synthesizers.

8. The calibration system of claim 6, further comprising:
a signal generator configured to generate frequency tones in a simultaneous and phase-coherent way.

9. The calibration system of claim 6, further comprising:
a signal generator configured to generate phase-coherent tones connected between the reference signal and an available input channel of the first system, in order to achieve a phase-coherent measurement of each generated tone by the first system.

10. The calibration system of claim 6, wherein the synthesizer circuit is part of the first system.

11. The calibration system of claim 10, wherein the first system comprises a stimulus-response system that includes a receiver device, and wherein the receiver device of the stimulus-response system is configured to operate phase-coherently with the synthesizer circuit.

12. The calibration system of claim 10, wherein the first system comprises a stimulus-response system that includes a receiver device, and wherein the synthesizer circuit is configured to operate phase-coherently with the receiver device of the stimulus-response system.

13. The calibration system of claim 6, wherein the processor circuit is part of the first system.

14. The calibration system of claim 6, wherein the first system comprises a stimulus-response system that includes a receiver device, and wherein the synthesizer circuit is part of the stimulus-response system.

15. The calibration system of claim 6,
wherein the first system comprises a receiver device; and
wherein in applying each generated tone to the first system, the processor circuit is configured to apply each generated tone to the receiver device.

16. The method of claim 1,
wherein the system comprises a receiver device; and
wherein said applying each generated tone to the system comprises applying each generated tone to the receiver device.

17. The method of claim 1,
wherein the system comprises a receiver device; and
wherein said measuring at least the respective phase of each generated tone using the system comprises measuring at least the respective phase of each generated tone using the receiver device.

18. The method of claim 1,
wherein the system comprises a stimulus-response system that includes a receiver device;
wherein said applying each generated tone to the system comprises applying each generated tone to the stimulus-response system.

19. The method of claim 1,
wherein the system comprises a stimulus-response system that includes a receiver device;
wherein said measuring at least the respective phase of each generated tone using the system comprises measuring at least the respective phase of each generated tone using the stimulus-response system.

20. A method for calibrating a receiver device or a stimulus-response system comprising a receiver device, the method comprising:
generating, by a synthesizer circuit, a set of calibration tones, comprising generating one tone of the set of calibration tones at a time with a repeatable known phase value and a different frequency value with respect to a most recent previously generated tone, and applying each generated tone to the receiver device or to the stimulus-response system one tone at a time;
generating, by the synthesizer circuit, a reference signal, which is phase-coherent with each generated tone, to measure each generated tone in a phase-coherent way with the receiver device or with the stimulus-response system;
measuring at least a respective phase of each generated tone using the receiver device or the stimulus-response system; and
determining, by a processor circuit, at least phase-related information for a set of calibration coefficients corresponding to the set of calibration tones comprising calculating a phase deviation of the measured respective phase from the repeatable known phase value for each generated tone.

21. A calibration system for calibrating a first system, said calibration system comprising:
a plurality of synthesizers configured to:
generate a set of calibration tones one tone at a time with a repeatable known phase value and a different frequency value with respect to a most recent previously generated tone; and
generate a reference signal which is phase-coherent with each generated tone; and
a processor in communication with the plurality of synthesizers, wherein the processor is configured to:
apply each generated tone to the first system, one tone at a time; and
determine at least phase-related information for a set of calibration coefficients corresponding to the set of calibration tones by calculating a phase deviation between a respective measured phase of each generated tone and the repeatable known phase value.

22. A method for calibrating a system, the method comprising:
applying, by a processor circuit, a set of calibration tones to the system one tone at a time, each of the calibration tones having a same known phase value and a different frequency value with respect to a previously generated tone;
generating, by a synthesizer circuit, a reference signal, which is phase-coherent with each generated tone, to measure each generated tone in a phase-coherent way with the system;
measuring at least a phase of each generated tone using the system; and
determining, by the processor circuit, at least phase-related information for a set of calibration coefficients corresponding to the set of calibration tones, comprising calculating a phase deviation of the measured phase from the same known phase value for each generated tone.

* * * * *